United States Patent [19]

Danielson et al.

[11] Patent Number: 5,474,526
[45] Date of Patent: Dec. 12, 1995

[54] DEVICE FOR THE CONNECTION OF FLUID CONDUITS FOR MEDICAL PURPOSES

[75] Inventors: Bo Danielson, Uppsala; Tore Magnusson, Knivsta; Laszlo Orban, Enköping; Torgny Petersson, Österbybruk, all of Sweden

[73] Assignee: Hemapure AB, Uppsala, Sweden

[21] Appl. No.: 87,787

[22] PCT Filed: Dec. 20, 1991

[86] PCT No.: PCT/SE91/00899

§ 371 Date: Aug. 17, 1993

§ 102(e) Date: Aug. 17, 1993

[87] PCT Pub. No.: WO92/13590

PCT Pub. Date: Aug. 20, 1992

[30] Foreign Application Priority Data

Jan. 30, 1991 [SE] Sweden .................................. 9100291

[51] Int. Cl.[6] .......................... A61M 39/00; A61M 37/00
[52] U.S. Cl. .............................. 604/4; 137/599.1; 604/30; 604/32; 604/248
[58] Field of Search ............................. 604/4–6, 29, 30, 604/32, 246–250; 137/599.1

[56] References Cited

U.S. PATENT DOCUMENTS

| | | | |
|---|---|---|---|
| T867,021 | 10/1969 | Carter | 604/32 |
| 4,405,320 | 9/1983 | Cracauer et al. | 604/175 |
| 4,496,350 | 1/1985 | Cosentino | 604/175 |
| 4,953,592 | 9/1990 | Takahashi et al. | 137/599.1 |

FOREIGN PATENT DOCUMENTS

| | | |
|---|---|---|
| 0299547 | 1/1989 | European Pat. Off. . |
| 0318358 | 5/1989 | European Pat. Off. . |
| 464665 | 5/1991 | Sweden . |
| WO88/01519 | 3/1988 | WIPO . |

Primary Examiner—Randall L. Green
Assistant Examiner—Rob Clarke
Attorney, Agent, or Firm—Jacobson, Price, Holman & Stern

[57] ABSTRACT

In a fluid conduit connecting device for medical purposes a housing and a connecting member, being connectable to the housing, carry cooperating sealing surfaces. For the purpose of protecting the sealing surfaces of the connecting member these surfaces are covered by protective surfaces of a protective member prior to the connection of the connecting member to the housing. Protective member is arranged to uncover the sealing surfaces when the connection into the housing takes place. The device is suitable particularly for connecting the blood stream of a patient to an external conduit and allows continuous arteriovenous hemofiltration.

22 Claims, 6 Drawing Sheets

DEVICE FOR THE CONNECTION OF FLUID CONDUITS FOR MEDICAL PURPOSES

BACKGROUND OF THE INVENTION

The invention concerns a fluid conduit connecting device for medical purposes, particularly for the connection of the blood circuit of a patient to an external circuit for blood filtering or other blood treatment.

A great number of patients today depend on blood filtering appliances. A common cause for this is acute renal failure, i.e. a non functional kidney system. Patients with this diagnosis may either receive a transplanted kidney or be treated with dialysis. Before transplantation comes into the question, the patient is however obliged to use dialysis. This is also the only solution for many patients due to the fact that transplantation is not feasible for one reason or the other and due to the shortage of kidneys available for transplantation. Thus, in Sweden today approximately 1600 patients are regularly treated with dialysis. This means a great strain, not only to the patients themselves, as it brings about frequent appearance at the hospital and stay at the premises during a period of at least three to four hours. It also brings about great costs for the society, the annual costs for one patient in dialysis may today be estimated to SEK 500 000. A very large part of the costs relate to personnel, equipment and premises and it is therefore desired to be able to conduct the treatment in the homes of patients, which would lead to great economic gain.

Of the different systems available today for conducting blood filtering one equipment may be mentioned which leads the blood from a blood vessel of the patient, transports it by means of an external pump through a blood treatment equipment and thereafter reinjects it into the patient.

Another solution is continuous ambulatory peritoneal dialysis, where an existing membrane in the body, which could be the abdominal membrane, is used. In this case blood is present on one side of the membrane, at the same time as a solution of salt and glucose, acting as a purifying liquid, is introduced to the other side of the membrane.

For the treatment of acute renal failure, continuous arteriovenous hemofiltration (CAVH) has recently been used. The principle of this method is continuous filtration of the blood, with the heart of the patient being used as the pump for pressing the blood through an external so called shunt circuit, wherein the blood is continuously filtered. After filtering the blood is reintroduced to the patient in a purified state.

All known systems to be the connected to the blood circuit of the patient are associated with drawbacks of different kinds. The problem of sterility is particularly serious, since all kinds of external equipment being connected to a patient bring about a risk of introducing infections into the blood circuit. As an example of a device for the connection of an external circuit to a blood circuit of a patent European Patent document No. EP-A2-0 087 189 could be mentioned, wherein an external member comprising two needles is inserted into a housing, through a self-sealing septum, the housing being transplanted into the body of the patient. The insertable needles of this device involve a substantial risk of introducing infections into the blood stream of the patient. In known types of shunt devices, conventional tube joints are used, being connected to inserted or transplanted connections for artery and vein respectively in the patient.

U.S. Pat. No. 4,496,350 describes a connecting device, where the needles are protected by a displaceable protective member for preventing the openings of the outer portions of the needles from exerting cutting action on the blood leakage preventing septum. Also this device brings about a great risk of introducing infections into the blood stream.

A different kind of connecting device is described in Swedish patent document No. SE-B-453 801 wherein a connecting half with artery or vein connections is implanted into the patient, and from the outside is connectable to an external circuit by means of an external connecting half, which is designed as a naked male portion, insertable into the implanted connecting half so as to allow CAVH-treatment.

In all these known devices the connections are unfortunately sources of infections that could be introduced into the patient despite the latter device comprising arrangements for sterilization.

There are also problems of sterility in connections of the external circuit and when connecting different sources of fluids to a patient.

BRIEF SUMMARY OF THE INVENTION

It is an object of the invention to provide a solution to the above mentioned problems and particularly to provide a connecting device allowing frequent CAVH-treatment of patients under maintained required hygienic standards. Further objects are to provide a connecting device which is easy to handle, economic in manufacture, tolerable by the patient and biocompatible.

These objects are accomplished by a device according to the present invention in a device which is particularly suitable for implantation into a patient with a portion of the housing extending outside the skin and allows the patient's own blood pressure to be used as a propellant to circulate the blood through an outer blood treatment circuit, e.g. a dialyser, and in a purified state, still using the patient's own blood pressure, reintroduce the blood to the blood stream of the patient under maintained sterility in the outer connecting member coming into contact with the housing. By thus protecting the connecting surfaces of the outer connecting member from coming into contact with the air or external objects before they are brought into cooperation with corresponding surfaces inside of the housing, there will be a radical reduction of the risk of infections.

Other objects are accomplished by further features according to the invention.

In one embodiment the outward coupling means may be closed in a simple manner at the same time as the connecting member is withdrawn from the housing.

In another embodiment the device is entirely or in part rotational symmetrically and the connection is achieved by rotation of the connecting member relative to the housing when it has been axially inserted into the housing.

In a further embodiment the housing is permanently carrying a valve member which may be displaced from an active position, where it directly connects the outward coupling means with each other to an inactive position, and where these are instead connected to the outer circuit via the connecting member. Through this embodiment no separate joining member is needed, since the joining function is obtained by the valve member being permanently seated within the housing. In this embodiment, the housing is preferably covered with a simple protective lid between treatments of the patient. This embodiment is however less suitable in connection with longer treatment periods due to the risk of coagulation within the connecting channel of the valve member in the inactive position.

A further feature facilitates the patient's skin to grow onto the implanted device.

Another feature allows the outward coupling means to be directly connected to each other between treatment periods as well as the possibility of allowing immediate access to the blood stream e.g. for medication purposes.

BRIEF DESCRIPTION OF THE DRAWINGS

The invention will now be explained in greater detail with reference to the appended drawings wherein.

DETAILED DESCRIPTION

Figure 1:
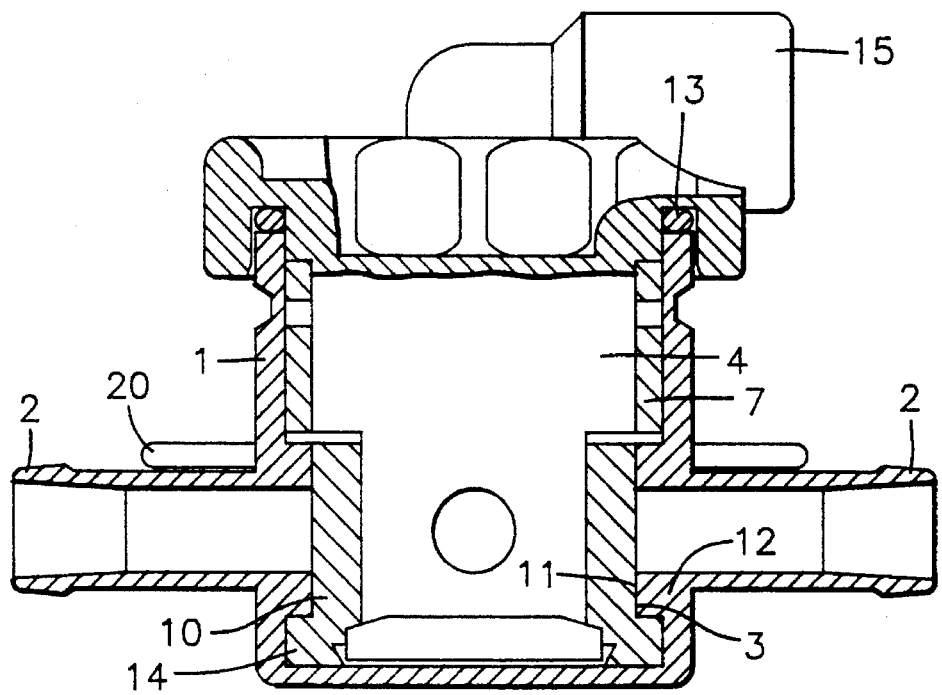
FIG. 1 is a cross-sectional view of the device according to the invention with the connecting member inserted into the housing member.
Figure 2A:
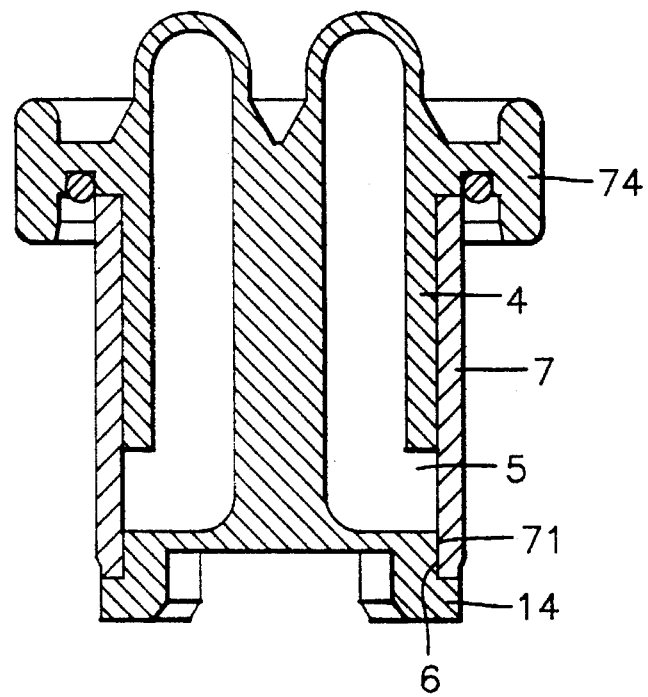
FIG. 2a is a vertical cross-sectional view of the connecting member with the protective member in protective position.
Figure 2B:
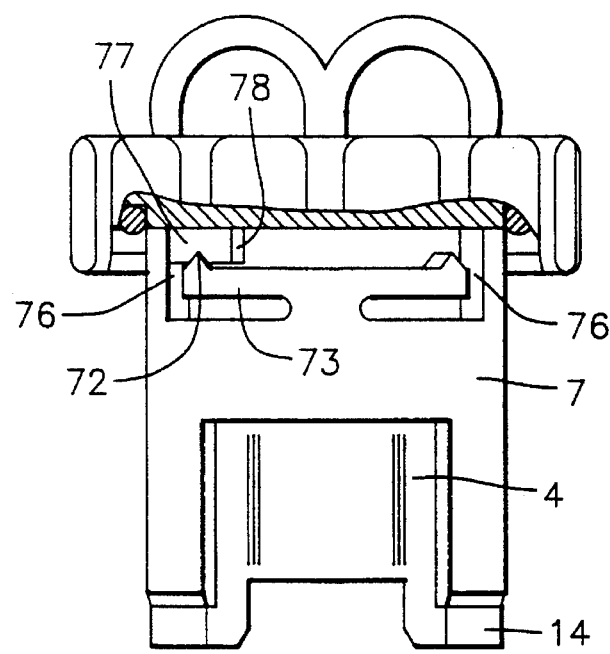
FIG. 2b is an elevational view of the connecting member of FIG. 2a partly in vertical cross-section.

FIG. 1 shows an essentially circular cylindric housing 1, with nipple-shaped outward coupling means, comprising artery and vein joints 2 when the housing is implanted into a human body. At the mouths of these coupling means within the housing, there are inward sealing surfaces 3 formed on inward thickened wall portions 12 in the housing, in the area of the artery and vein joints. A partly cylindrical replaceable valve member 10 is inserted within the housing and cooperates by means of valve surfaces 11 with the inward sealing surfaces 3 of the housing in the position shown in FIG. 1. The artery and vein joints are shown closed. The valve member 10 is at its lower end (at the bottom in FIG. 1) provided with guide ribs 14, by which it is held in the shown axial position by the thickened wall portions 12. Further, a connecting member 4 is inserted into the housing 1. This connecting member 4 which is shown separately in FIGS. 2a and b, carries a protective sleeve 7 on its cylindrical mid-portion, between a protective cover 74 and guide ribs 14 (FIG. 2a). The protective sleeve 7 will thus be rotatable around the connecting member 4 but axially fixed to the latter. The protective sleeve 7 is provided with protective surfaces 71, protecting and covering outward sealing surfaces 6 of the connecting member 4. First and second openings 5 of the connecting member 4, communicating with the outer circuit through channels in the connecting member 4, are thus closed in the position shown in FIG. 2a. The protective sleeve 7 is cut in its lower portion (at the bottom in the figures, c.f. FIG. 2b) so as to occupy at the most 90° in the rotational direction in the area of each of the outward sealing surfaces 6 of the connecting member.

Thus, the protective sleeve 7 is in the position shown in FIG. 2a with respect to the connecting member 4 when this member is inserted into the position according to FIG. 1. From this position the connecting member is rotated 90° to reach the position shown in FIG. 3, whereby the first and second openings 5 of the connecting member 4 will communicate with the artery and vein coupling means 2 so that the latter will be connected to the external circuit via conduit joints 15 or the like (at the top in FIG. 3). During rotation of the connecting member 4 from the position according to FIG. 1 to the position according to FIG. 1 to the position according to FIG. 3, the protective sleeve 7 is prevented from rotating by the inward thickened wall portions 12. The outward sealing surfaces 6 of the connecting member 4 thus will instead lie close to the corresponding sealing surfaces 3 of the housing 1. When the connecting member 4 is in the position according to FIG. 3 it is, besides being axially fixed to the housing through cooperation between the guide ribs 14 and the lower surfaces of the thickened wall portions, also sealed by the sealing ring 13.

Figure 3:
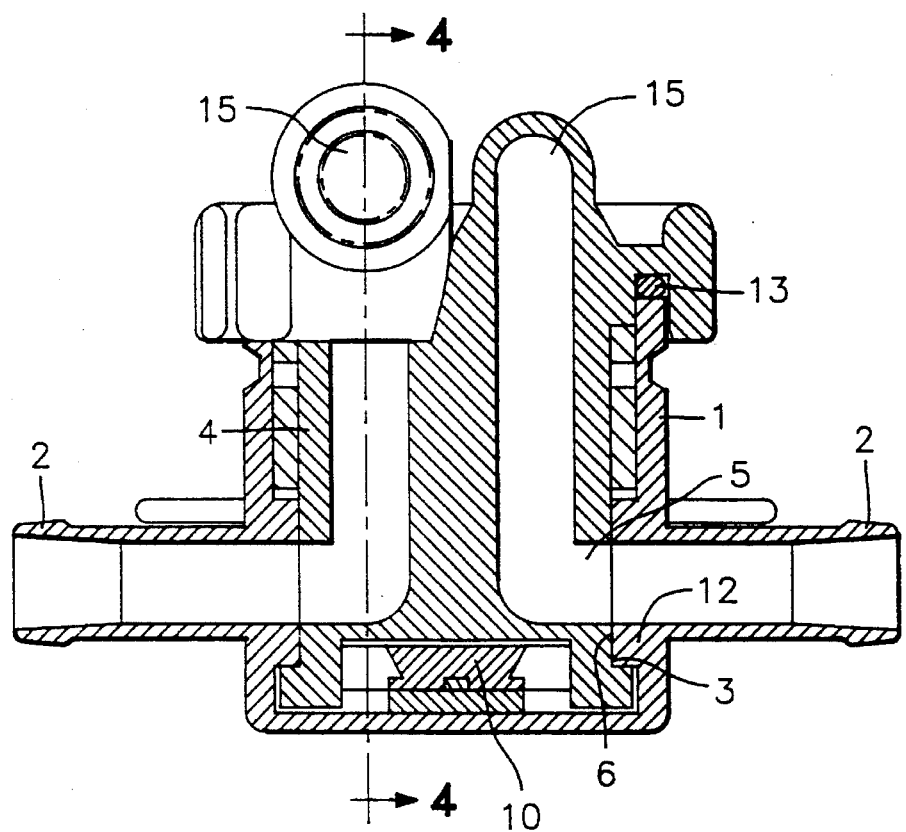
FIG. 3 is a vertical partly cross-sectional view of the device according to the invention with the connecting member in a connected position.
Figure 4:
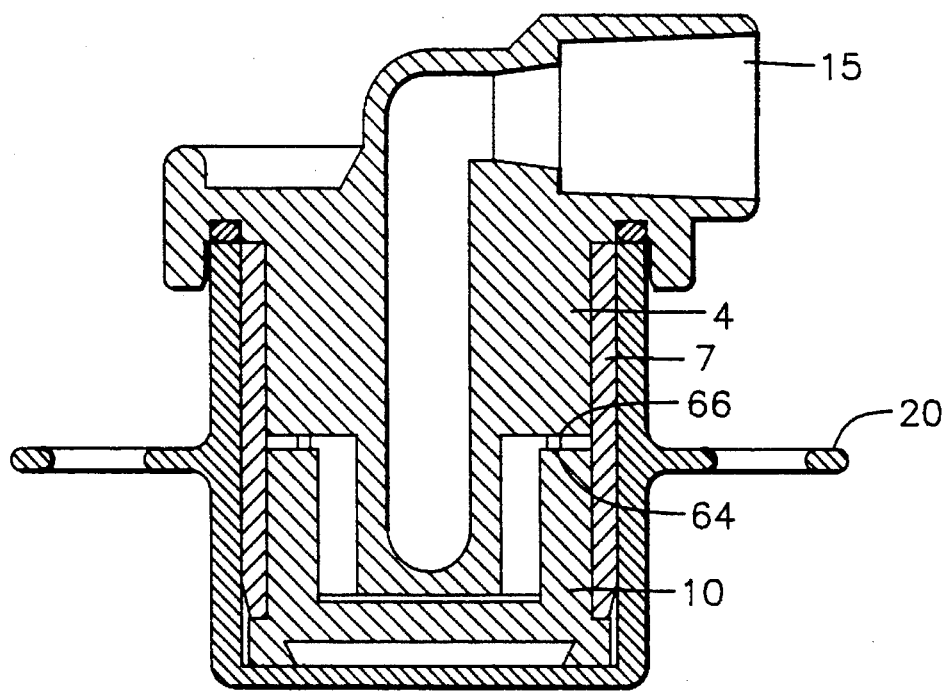
FIG. 4 is a cross-sectional view taken along line 4—4 of FIG. 3.

In FIG. 4 the device is shown in a section perpendicular to the section according to FIG. 3 with the connecting member in a connected position with respect to the housing. The protecting sleeve 7 is in the same position as in FIG. 1. The valve member 10 is coupled for rotational cooperation with the connecting member when the latter is inserted into the housing. Finally FIG. 4 shows a so called implanting flange 20, surrounding the cylindrical wall of the housing and being adapted to be located directly below the skin of the patient. The implanting flange 20 will facilitate the growth of the skin of the patient onto the device. The implanting flange allows a certain movement of the housing with respect to the skin of the patient without the appearance of "gaps" at the implanted housing.

Figure 5:
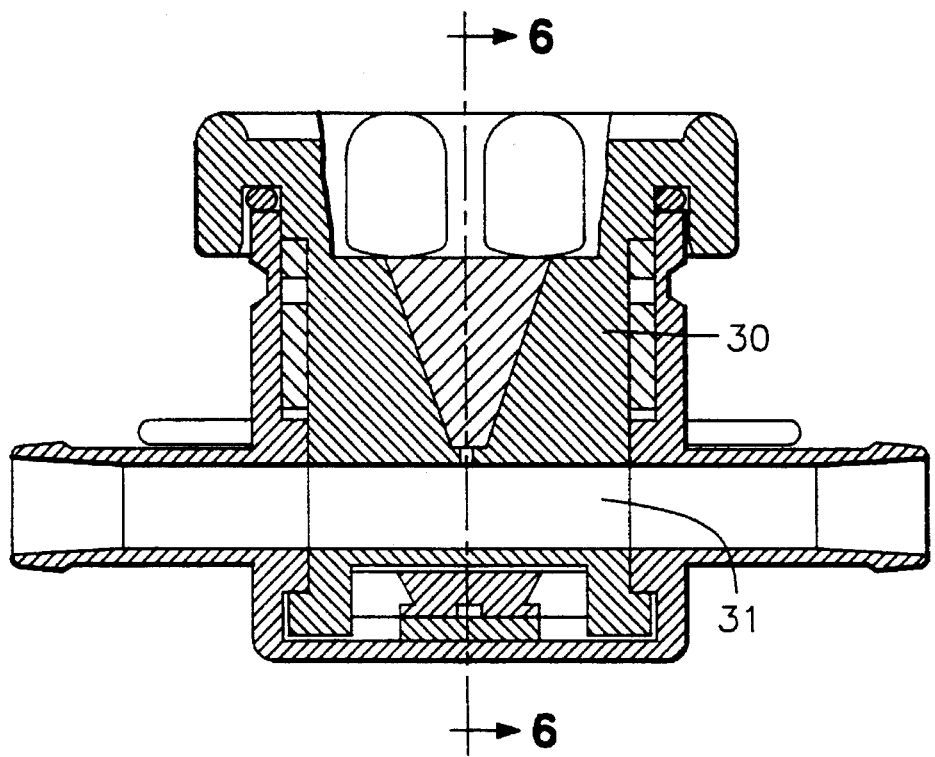
FIG. 5 is a vertical cross-sectional view showing the joining member in its inserted position.

FIG. 5 shows the cooperation of a separate joining member, or second connecting member, 30 with the housing 1 in a normal position (with connecting member 4 removed), i.e. when the patient is not subject to blood treatment. This joining member 30 comprises a preferably straight channel 31, which directly connects the artery and vein coupling means with each other. Further the joining member 30 also carries a protective sleeve to protect the outward sealing surfaces from external influences. The joining member is inserted into the housing in the same way as the connecting member as described above.

Figure 6:
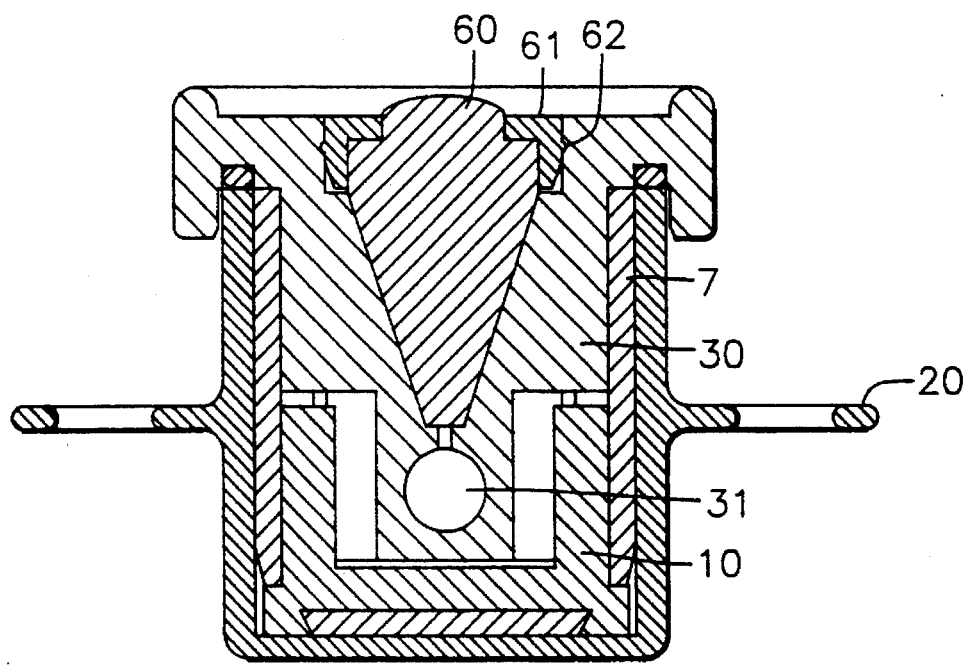
FIG. 6 is a cross-sectional view taken along line 6—6 of FIG. 5.

FIG. 6 shows the housing with inserted joining member 30 in a cross-section of FIG. 4. The joining member 30 here carries a penetrable septum, which is comprised of a silicon rubber element 60, between the channel 31 and the outside. Hereby an immediate introduction to the blood stream of substances, as e.g. medical compounds, is possible by penetrating the septum, with a needle or the like. The member 60 is fixed by means of a fixing plate 61, which cooperates with a slot in the joining member with its rib 62.

Figure 7A:
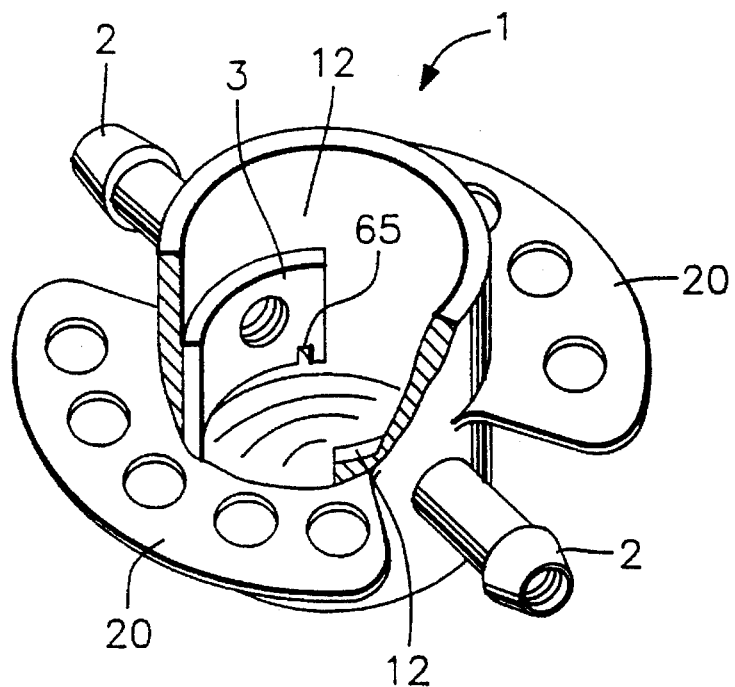
FIG. 7a is a perspective view of the housing partly broken away.

FIG. 7a thus shows a perspective partly sectional view of the housing 1. The figure shows the thickened wall portions 12 with inward sealing surfaces 3 in the areas of the mouths of the artery and vein coupling means within the essentially cylindrical housing. Further the implanting flanges 20 are shown.

Figure 7B:
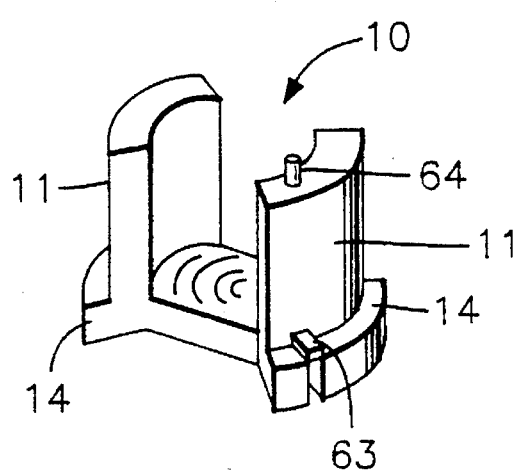
FIG. 7b is a perspective view showing the valve member.

FIG. 7b shows the valve member 10 with valve surfaces 11 and guide ribs 14. To enable the valve member 10 to be locked in rotational direction in the closing position within the housing 1, it is provided with one or more arresting projections 63, which cooperate(s) with arresting recesses 65 in the thickened wall portions of the housing 1 (see FIG. 7a). Each arresting projection 63 is linked to a pressure pin 64 which may be actuated by surfaces 66 of the joining member or the connecting member respectively (see FIG. 4). This actuation is accomplished when inserting, by the surfaces 66, via the pressure pin 64 pressing the arresting projection 63 downwards thereby freeing it from cooperation with the arresting recess 65, and thus freeing the valve body for rotational movement.

Figure 7D:
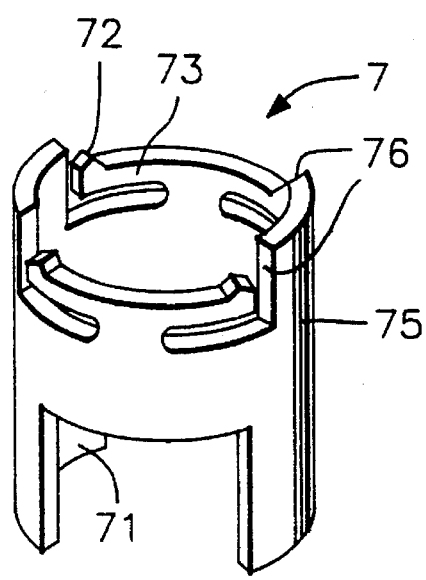
FIG. 7d is a perspective view of the protective sleeve.
Figure 7C:
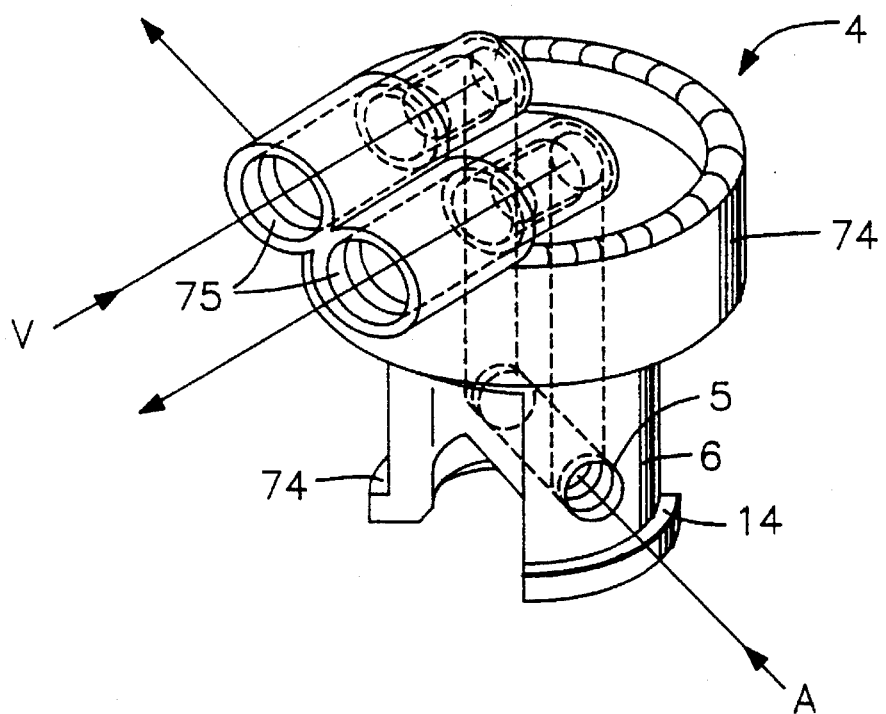
FIG. 7c is a perspective view of the connecting member.

FIG. 7c shows the connecting member 4 without a protective sleeve. The arrows A and V respectively indicate the direction of the blood flow from the artery coupling means to the vein coupling means. The connecting member 4 is provided with a protective cover 74 for sealing the upper part of housing 1. Further dashed lines indicate how the first and second openings 5 communicate with the joints 15 of the external circuit. The outward sealing surfaces 6 are located in the area around the first and second openings 5. Finally the connecting member 4 comprises guide ribs 14 at its lower portion for cooperation with the housing in a previously described manner.

FIG. 7d shows the protective sleeve 7 with one of the protective surfaces 71. At is upper part, the protective sleeve 7 is provided with projections 72 on resilient portions 73, said projections cooperating with recesses in protrusions 77 of the connecting member and the joining member, respectively (see FIG. 2b). Said projections and recesses allow snap-in arrestment in a distinct rotational position to be obtained between the protective sleeve 7 and the connecting member 4 and the joining member 30, respectively. Further the protective sleeve 7 on its upper part is provided with portions 75, the side surfaces 76 of which cooperate with surfaces 78 of said protrusions 77 for limiting the mutual rotation between the connecting member/joining member and the protective sleeve.

Due to this limitation and snap-in arrestment, safe control of the connection of the connecting member/joining member into the housing is achieved.

Figure 7E:
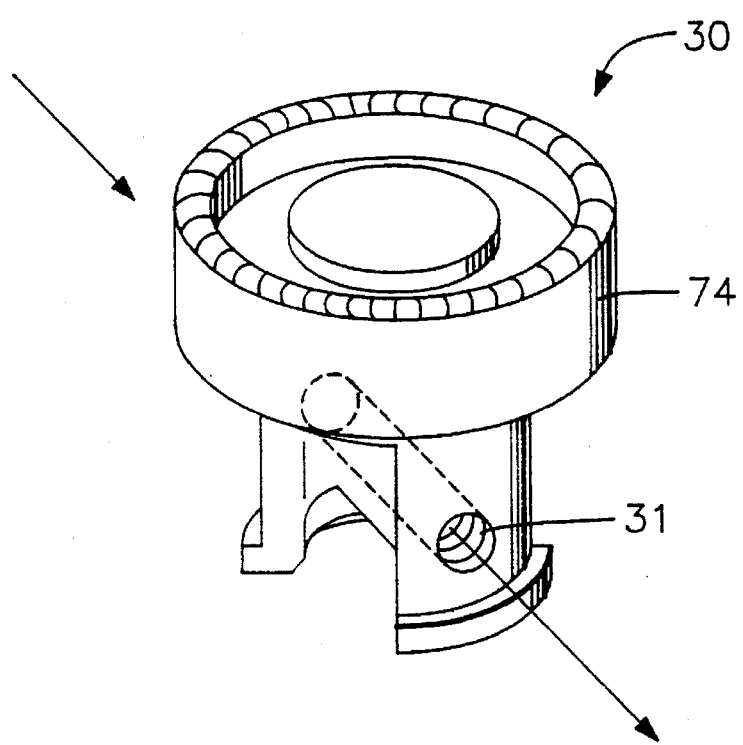
FIG. 7e is a perspective view of the joining member.

FIG. 7e shows the joining member 30 with channel 31 and the protective cover 74.

To be able to place a protective sleeve 7 e.g. on a connecting member 4 the protective cover 74 (or possibly the guiding ribs) constitutes a separate fastenable part of the connecting member 4. After having placed the protective sleeve 7 onto the lower part of the connecting member 4, the protective cover 74 may be fastened to said lower part in any suitable manner e.g. by glueing.

Figure 8:
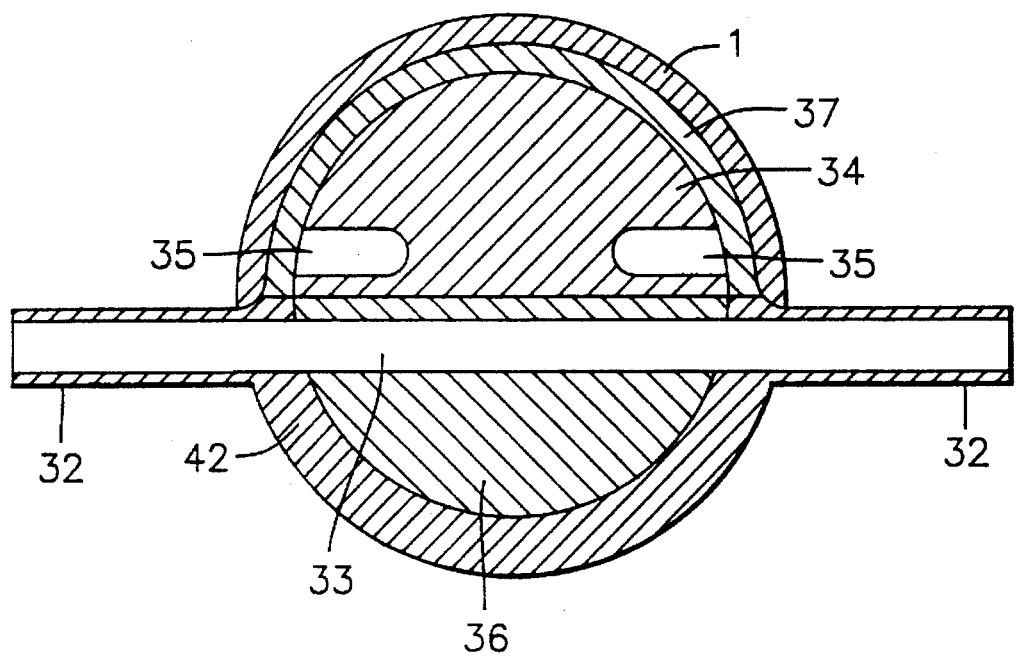
FIG. 8 is a horizontal cross-sectional view of an alternative embodiment of the invention.

FIG. 8 shows an alternative embodiment with a specially shaped valve member. A housing 1 is thus shown with artery and vein coupling means 32. The housing 1 is in this case provided with one single thickened inward wall portion 42, on the inside of which the inward sealing surfaces are located. A connecting member 34 is inserted into the housing and comprises first and second openings 35, which communicate with the outer circuit. Further the connecting member 34 carries a protective sleeve 37, which protects the one and only outward sealing surface of the connecting member 34 in the position shown in the figure. A valve member 36 with a channel 33 provides the desired connection of the artery and vein coupling means 32 (in the position shown in the figure) when the patient is not subject to treatment. For the connection of the artery and vein coupling means to the outer circuit, the connecting member 34 is rotated 180°, whereby the first and second openings 35 will be placed right in front of the mouths of the artery and vein coupling means 32 within the housing 1. The protecting sleeve 37 is stopped in the shown position by its cooperation with the thickened inward wall portion 42.

Further modifications are of course possible within the scope of the invention. For example, the protective surfaces may be arranged to free the sealing surfaces in any other way than by rotation of a connecting member with respect to a protective sleeve. The protective member thus does not have to be rotational symmetrically and may alternatively free the surfaces through axial displacement. The sealing surfaces may also take up relatively smaller dimensions than as has been shown in the embodiments. The channels of the connecting member and (where appropriate) in the valve member may have another line up than the shown. The housing may also be of any other shape than cylindrical, e.g. box-shaped. If the device is rotational symmetrically the locking of the connecting member/joining member within the housing may be accomplished in any other suitable manner than shown, e.g. by a conventional bayonet-mount in the area of the protective lid. Thereby exact positioning in rotational direction will be easily achieved.

The housing is produced from a material suitable for implanting, particularly titanium, which is well documented in similar applications and has been found tissue compatible. The artery and vein coupling means may consist of PTFE or any other suitable material. The other details, as connecting members etc. are to be regarded as disposable equipment and is thrown away after use. This generally also applies to all the other equipment of the external circuit, including the artificial kidney.

The device may also be adapted for other kinds of blood treatment. Alternative uses which may be mentioned, are infusion e.g. total parenteral nutrition, (TPN), blood stream sapling, heart failure treatment, gas exchange as oxygenizing, cytostatic treatment as well as the connection of artificial organs e.g. pancreas. Further a number of other kinds of blood filtering or blood treatments as e.g. plasma transfusion, plasmolysis, immunoadsorbtion, cell separation and cell treatment.

Finally, the connecting device according to the invention is also very suitable for use as an advanced conduit coupling for a number of medical purposes where a high hygienic standard is demanded. In these cases the housing is thus not implanted into a patient but is part of an external circuit e.g. in connection with catheters to gain access to the blood stream or different cavities in the organism, as well as to introduce different substances into the external circuit. The housing may hereby be modified in such a way that it does not comprise details concerning its use as an implant. Another possible modification consists in that only one outward coupling means extends from the housing.

We claim:

1. A fluid conduit connecting device for medical purposes for connecting in the blood circuit of a patient, said connecting device comprising:

a housing having an interior chamber;

two coupling means extending outwardly from said housing for connecting to the blood circuit of a patent;

a first connecting member insertable into said housing chamber;

a protective member mounted on said first connecting member in relative movable relationship therewith;

inward sealing surfaces on the inside of said housing between said first connecting member and said housing;

first channels in said coupling means having inner end portions extending through said housing and said inner sealing surfaces for communication with the interior chamber of said housing;

first and second openings in said first connecting member each having one end positionable for communicating respectively with one of said first channels of said two coupling means and another end opening outwardly of said first connecting member and said housing for connecting with an external circuit including equipment for blood treatment;

at least one outward sealing surface on said first connecting member engageable in sealing relationship with said inward sealing surfaces on said housing in areas surrounding said one ends of said first and second openings and said inner end portions of said first channels;

said movable protective member having at least one protective surface thereon in relative movable engagement with said at least one outward sealing surface on said first connecting member for protecting said at least one outward sealing surface from the external ambient environment when said first connecting member is not inserted into said housing, said protective member being insertable into said housing chamber when said first communicating member is inserted into said housing chamber for cooperative relationship between said inward sealing surfaces on said housing and said at least one outward sealing surface on said first connecting member for obtaining a leak proof connection between said first and second openings and said inner end portions of said first channels; and valve means movably mounted within said housing for adjustment therein between a first position for closing said first channels in said outward coupling means and a second position for opening said first channels in said outward coupling means, said valve means comprising a valve member having valve surfaces engageable with said inward sealing surfaces on said housing in said first position and disengageable from said inward sealing surfaces in said second position.

2. The device as claimed in claim 1 where in:

said inward sealing surfaces in said housing are cylindrical;

said at least one outward sealing surface comprises cylindrical outward sealing surfaces on said first connecting member;

said protective surfaces on said protective member are cylindrical; and said valve surfaces are cylindrical.

3. The device as claimed in claim 2 wherein:

said protective member comprises a cylindrically-shaped sleeve rotatably mounted on said first connecting member; and means are provided for preventing relative axial movement of said protective member with respect to said first connecting member.

4. The device as claimed in claim 3 wherein:

said housing is substantially cylindrical;

said first connecting member is substantially cylindrical so that said first connecting member is rotatable when inserted in said housing chamber; and at least one inward thickened portion is provided on said housing, said at least one inward thickened portion having said inward sealing surfaces thereon, and said inward thickened portion further comprises means for preventing rotation of said protective member when said first connecting member is rotated within said housing chamber to a connecting position where said first and second openings communicate with said first channels in said outward coupling means.

5. The device as claimed in claim 4 and further comprising:

at least one resilient arresting projection extending outwardly from said valve body; and at least one arresting recess in said thickened wall portion for receiving said arresting projection in cooperating relationship for locking said valve body rotationally in a closing position.

6. The device as claimed in claim 5 wherein:

said inward sealing surfaces in said housing are cylindrical;

said outward sealing surfaces on said second connecting member are cylindrical;

said protective surfaces on said second protective member are cylindrical; and said valve surfaces are cylindrical.

7. The device as claimed in claim 6 wherein:

said second protective member comprises a cylindrically-shaped sleeve rotatably mounted on said second connecting member; and means are provided for preventing relative axial movement of said second protective member with respect to said second connecting member.

8. The device as claimed in claim 7 wherein:

said housing is substantially cylindrical;

said second connecting member is substantially cylindrical so that said second connecting member is rotatable when inserted in said housing chamber; and at least one inward thickened portion is provided on said housing, said at least one inward thickened portion having said inward sealing surfaces thereon, and further comprises means for preventing rotation of said second protective member when said second connecting member is rotated within said housing chamber to a connecting position where said opposite ends of said passage communicate respectively with said first channels in said coupling means.

9. The device as claimed in claim 6 wherein:

said inward sealing surfaces are substantially diametrically opposed and extend a maximum of 90° in the direction of rotation of said second connecting member;

said outward sealing surfaces are substantially diametrically opposed and extend a maximum of 90° in the direction of rotation of said second connecting member; and said protective surfaces on said second protective member are substantially diametrically opposed and extend a maximum of 90° in the direction of rotation of said second protective member.

10. The device as claimed in claim 2 wherein:

said inward sealing surfaces are substantially diametrically opposed and extend a maximum of 90° in the direction of rotation of said first connecting member;

said outward sealing surfaces are substantially diametrically opposed and extend a maximum of 90° in the direction of rotation of said first connecting member; and said protective surfaces are substantially diametrically opposed and extend a maximum of 90° in the direction of rotation of said protective member.

11. The device as claimed in claim 2 wherein:

said protective member comprises a cylindrically-shaped sleeve mounted on said first connecting member for axial displacement with respect to said first connecting member.

12. The device as claimed in claim 1 wherein:

said protective member is displaceable on said first connecting member for uncovering said outward sealing surfaces by axial displacement with respect to said connecting member.

13. The device as claimed in claim 1 and further comprising:

flanges on said housing extending outwardly therefrom so to facilitate implanting said housing in a patient in the area of the skin level of the patient so that the skin of the patient will grow onto said flanges.

14. The device as claimed in claim 1 and further comprising:

a second connecting member insertable into said housing chamber interchangeably with said first connecting member so that said inward sealing surfaces on the inside of said housing are between said second connecting member and said housing;

a second protective member mounted on said second connecting member in relative movable relationship therewith;

a passage in said second connecting member having opposite ends positionable for communicating respectively with one of said inner end portions of said first channels;

said at least one outward sealing surface comprising outward sealing surfaces on said second connecting member engageable in sealing relationship with said inward sealing surfaces on said housing in areas surrounding said opposite ends of said passage and said inner end portions of said first channels; and protective surfaces on said second movable protective member in relative movable engagement with said outward sealing surfaces on said second connecting member for protecting said outward sealing surfaces on said second connecting member from the external ambient environment when said second connecting member is not inserted into said housing, said second protective member being insertable into said housing chamber when said second connecting member is inserted into said housing chamber for cooperative relationship between said inward sealing surfaces on said housing and said outward sealing surfaces on said second connecting member for obtaining a leak proof connection between said passage and said inner end portions of said first channels.

15. The device as claimed in claim 14 wherein:

said second protective member is displaceable on said second connecting member for uncovering said outward sealing surfaces by displacement with respect to said second connecting member.

16. The device as claimed in claim 14 and further comprising:

flanges on said housing extending outwardly therefrom to facilitate implanting said housing in a patient in the area of the skin level of the patient so that the skin of the patient will grow onto said flanges.

17. The device as claimed in claim 14 and further comprising:

at least one resilient arresting projection extending outwardly from said valve body; and at least one arresting recess in said thickened wall portion for receiving said arresting projection in cooperating relationship for locking said valve body rotationally in a closing position.

18. The device as claimed in claim 14 and further comprising:

a penetrable septum in said second connecting member between said passage and the outside of said device to facilitate injection of medical substances directly into blood flowing through said passage.

19. The device as claimed in claim 1 wherein:

said valve means comprises a valve body having passage means therein for directly connecting said outward coupling means with each other in said second position; and means are provided on said first connecting member for displacing said valve body to said first position when said first connecting member is inserted into said housing chamber for obtaining said leakproof connection.

20. The device as claimed in claim 19 wherein:

said protective member comprises a cylindrically-shaped sleeve rotatably mounted on said first connecting member; and means are provided for preventing relative axial movement of said protective member with respect to said first connecting member.

21. The device as claimed in claim 19 wherein:

said housing is substantially cylindrical;

said first connecting member is substantially cylindrical so that said first connecting member is rotatable when inserted in said housing chamber; and at least one inward thickened portion is provided on said housing, said at least one inward thickened portion having said inward sealing surfaces thereon, and said inward thickened portion further comprises means for preventing rotation of said protective member when said first connecting member is rotated within said housing chamber to a connecting position where said first and second openings communicate with said first channels in said outward coupling means.

22. The device as claimed in claim 1 wherein:

said protective member is mounted on said first connecting member for relative axial displacement with respect to said first connecting member.

* * * * *